US008978477B2

(12) United States Patent
Nyholt (10) Patent No.: US 8,978,477 B2
(45) Date of Patent: Mar. 17, 2015

(54) LINEARLY-TRAVELLING ULTRASONIC PROBE MOUNT AND METHODS FOR USE

(75) Inventor: John James Nyholt, Seabrook, TX (US)

(73) Assignee: BP Corporation North America Inc., Houston, TX (US)

( * ) Notice: Subject to any disclaimer, the term of this patent is extended or adjusted under 35 U.S.C. 154(b) by 379 days.

(21) Appl. No.: 13/462,989

(22) Filed: May 3, 2012

(65) Prior Publication Data

US 2012/0285249 A1 Nov. 15, 2012

Related U.S. Application Data (60) Provisional application No. 61/484,539, filed on May 10, 2011.

(51) Int. Cl.
| | | |
|---|---|---|
| *G01N 29/04* | (2006.01) | |
| *G01N 29/265* | (2006.01) | |
| *G01N 29/22* | (2006.01) | |

(52) U.S. Cl.
CPC ............ *G01N 29/265* (2013.01); *G01N 29/226* (2013.01)
USPC .......................................................... 73/620

(58) Field of Classification Search
USPC ............... 73/620, 622, 623, 634, 644, 152.02
See application file for complete search history.

(56) References Cited

U.S. PATENT DOCUMENTS

| | | | |
|---|---|---|---|
| 3,575,043 A * | 4/1971 | Allen et al. ...................... 73/619 |
| 4,472,346 A | 9/1984 | Takeda et al. |
| 4,586,379 A | 5/1986 | Burkhardt, Jr. |
| 4,991,441 A * | 2/1991 | Nottingham et al. ........... 73/633 |
| 5,047,990 A * | 9/1991 | Gafos et al. ........................ 367/6 |
| 5,652,387 A * | 7/1997 | Dumont et al. .................. 73/622 |
| 5,661,242 A * | 8/1997 | Schreiner et al. ............... 73/623 |
| 6,220,099 B1 | 4/2001 | Marti et al. |
| 8,459,196 B2 * | 6/2013 | Provencher et al. ........... 114/222 |
| RE44,935 E * | 6/2014 | Provencher et al. ........... 114/222 |
| 2010/0011864 A1 | 1/2010 | Hanan et al. |

FOREIGN PATENT DOCUMENTS

| | | |
|---|---|---|
| DE | 202007014951 U1 | 1/2008 |
| FR | 2861457 | 4/2005 |

OTHER PUBLICATIONS

PCT International Search Report and the Written Opinion of the International Searching Authority, or the Declaration, mailed on Jul. 31, 2012, in related International application No. PCT/US2012/036378, 12 pages.

* cited by examiner

*Primary Examiner* — J M Saint Surin
(74) *Attorney, Agent, or Firm* — John L. Wood (57) ABSTRACT

A device for conducting an ultrasonic inspection of an object of interest comprises a base member. In addition, the device comprises a track coupled to the base member. Further, the device comprises a carriage moveably coupled to the track. Still further, the device comprises a drive system coupled to the carriage and configured to move the carriage linearly along the track. Moreover, the device comprises an ultrasonic probe coupled to the carriage.

20 Claims, 9 Drawing Sheets

LINEARLY-TRAVELLING ULTRASONIC PROBE MOUNT AND METHODS FOR USE

CROSS-REFERENCE TO RELATED APPLICATIONS

This application claims benefit of U.S. provisional patent application Ser. No. 61/484,539 filed May 10, 2011, and entitled "Linearly-Travelling Ultrasonic Probe Mount and Methods for Use," which is hereby incorporated herein by reference in its entirety.

STATEMENT REGARDING FEDERALLY SPONSORED RESEARCH OR DEVELOPMENT

Not Applicable.

BACKGROUND

1. Field of Technology

This disclosure relates generally to ultrasonic inspection techniques and, more particularly, to apparatus and methods to perform subsea ultrasonic inspections.

2. Background Information

Ultrasound is a form of cyclical sound energy that travels as a waveform through a conducting medium (e.g., metal, liquid, body tissue, etc.). The frequency of an ultrasonic wave is above 20,000 Hz (or 20 KHz), generally greater than the upper threshold of human hearing.

The basic principles enabling ultrasonic technologies to be employed in inspection and diagnostic procedures are well-understood. Activating an ultrasonic probe (i.e. a device including a transmitter and a receiver of ultrasonic energy) positioned adjacent to the outer surface of an object of interest allows an image to be formed showing components internal to the object of interest. The ultrasonic wave is generated when an electric field is applied to one or more piezoelectric crystals located in the probe. Electrical stimulation causes mechanical distortion of the crystals causing them to vibrate and thereby produce sound waves (i.e. mechanical energy). An ultrasound image is generated when the pulsed sound waves emitted from the probe are transmitted into the object of interest, reflected off the interfaces of differing materials, and returned to the probe. The piezoelectric crystals of the probe, upon receiving the returning wave (i.e. echo), vibrate in response, and a transducer in the probe converts the mechanical energy from the vibrating crystals into an electrical signal, which is then processed and displayed as an image on a display screen.

A very common application of ultrasonic technologies is in the medical field where ultrasound enables a physician to visually observe the condition of a fetus, as well as tissue and other features internal to a patient's body. Due to its ability to image and display internal components of an object of interest, ultrasonic technologies have likewise been employed in the analysis and non-destructive testing of engineered structures, machines and other man-made products.

Subsea pipelines, products and structures associated with offshore oil and gas operations periodically require inspection and analysis. These objects may be located at the sea floor which, in some instances, may be 5,000-7,000 feet or more below the surface. At such depths, the water pressure exceeds 2,000 psi. Such depths and pressures may present difficult conditions in which to attempt ultrasonic inspection, and consequently, render some conventional equipment ineffective. For example, divers are unable to work at such depths, making the use of handheld ultrasonic probes impossible. Thus, carrying out ultrasonic inspection at such depths requires system components be carried to the sea floor and positioned by deep diving, remotely operated vehicles (ROV's) controlled by an operator at the surface. Not only may conventional ultrasonic technologies, systems and components be unable to withstand the extreme subsea pressures encountered, but the components may be too fragile to be handled by the manipulating arms of the ROV. Further, accurately controlling the ROV from substantial distances, and using the ROV and its mechanical arms to position and operate components of conventional ultrasonic apparatus and systems, is impractical in many instances.

Accordingly, there remains a need in the art for improved devices and methods for employing ultrasonic inspection technologies subsea. Such devices and methods would be particularly well received if they offer the potential for use by subsea ROVs to ultrasonically inspect deepwater components.

BRIEF SUMMARY OF THE DISCLOSURE

These and other needs in the art are addressed in one embodiment by a device for conducting an ultrasonic inspection of an object of interest. In an embodiment, the device comprises a base member. In addition, the device comprises a track coupled to the base member. Further, the device comprises a carriage moveably coupled to the track. Still further, the device comprises a drive system coupled to the carriage and configured to move the carriage linearly along the track. Moreover, the device comprises an ultrasonic probe coupled to the carriage.

These and other needs in the art are addressed in another embodiment by a method for conducting a subsea ultrasonic inspection of an object of interest. In an embodiment, the method comprises (a) deploying an ultrasonic inspection device subsea. The device includes a base member and an ultrasonic probe moveably coupled to the base member. In addition, the method comprises (b) positioning the probe adjacent to the object of interest. Further, the method comprises (c) emitting a first ultrasonic waveform from the ultrasonic probe into the object of interest. Still further, the method comprises (d) moving the probe linearly relative to the base member and the object of interest. Moreover, the method comprises (e) emitting a second ultrasonic waveform from the probe into the object of interest after (c) and (d).

These and other needs in the art are addressed in another embodiment by an apparatus for performing ultrasonic inspections. In an embodiment, the apparatus comprises a base member having a longitudinal axis, a first end, a second end opposite the first end, an upper surface extending between the first end and the second end, and a lower surface extending between the first end and the second end. In addition, the apparatus comprises an elongate track mounted to the upper surface of the base member and oriented parallel to the longitudinal axis. Further, the apparatus comprises a carriage assembly moveably coupled to the track. Still further, the apparatus comprises a drive system coupled to the carriage assembly and configured to move the carriage assembly along the track. Moreover, the apparatus comprises a probe suspension system moveably coupled to the carriage assembly. The probe suspension system including a probe holder biased away from the carriage assembly. The apparatus also comprises an ultrasonic probe mounted to the probe holder.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the disclosed embodiments of the invention, reference will now be made to the accompanying drawings in which.

DETAILED DESCRIPTION OF DISCLOSED EMBODIMENTS

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 1:
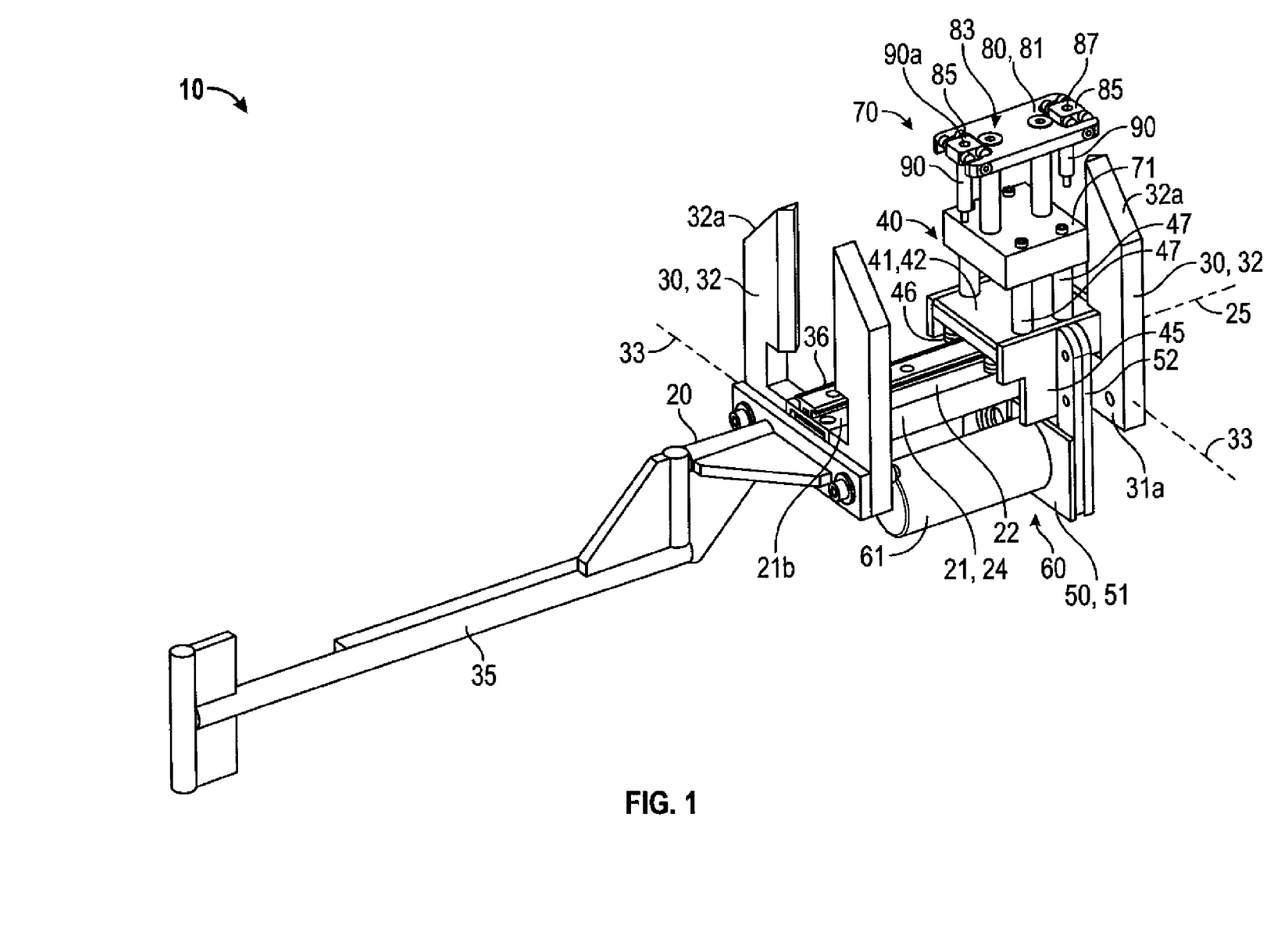
FIG. 1 is a perspective view of an embodiment of an ultrasonic inspection device in accordance with principles described herein.
Figure 2:
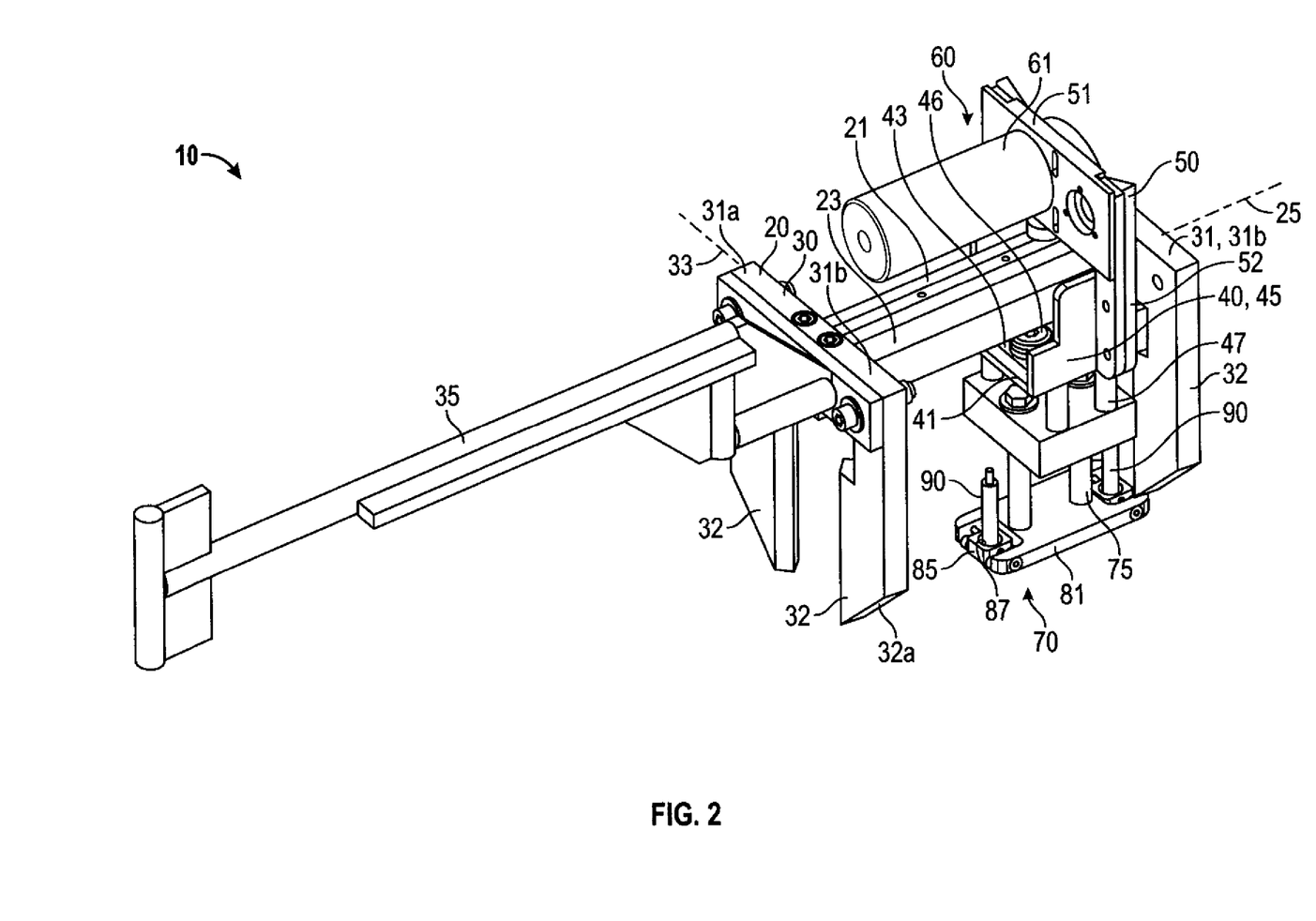
FIG. 2 is another perspective view of the ultrasonic inspection device of FIG. 1.

Referring now to FIGS. 1 and 2, an embodiment of an ultrasonic inspection device 10 is shown. As will be described in more detail below, device 10 is particularly suited for use subsea where it can be positioned and manipulated by one or more subsea ROVs. In this embodiment, device 10 includes a probe holding device or mount 20 and a pair of ultrasonic probes 90 coupled thereto. Mount 20 is used to position and manipulate probes 90 for ultrasonic inspection of an object of interest.

Referring now to FIGS. 1-4, in this embodiment, mount 20 includes a base 21, a carriage assembly 40 moveably coupled to base 21, a drive system 60 configured to drive the movement of carriage assembly 40 along base 21, and a probe suspension system 70 coupled to carriage assembly 40. Base 21 is an elongate rigid support member having a central or longitudinal axis 25, a first end 21a, a second end 21b opposite end 21a, an upper planar surface 22 extending between ends 21a, b, a lower planar surface 23 extending between ends 21a, b, and a pair of lateral planar side surfaces 24 extending between surfaces 22, 23 and ends 21a, b. In this embodiment, base 21 has a rectangular cross-section taken perpendicular to axis 25.

An end plate 30 is attached to each end 21a, b of base 21. Each end plate 30 is a rigid generally U-shaped structure including a base 31 and a pair of parallel arms or standoffs 32 extending perpendicularly from base 31. In particular, base 31 has a central or longitudinal axis 33 oriented perpendicular to axis 25 of base 21, a first end 31a, a second end 31b opposite end 31a, and a recess or notch 34 axially centered between ends 31a, b. Notch 34 in each end plate 30 receives one end 21a, b of base 21. One standoff 32 extends perpendicularly from each end 31a, b, and generally upward and away from upper surface 22 of base 21. In this embodiment, standoffs 32 are orthogonal to bases 21, 31. The end of each standoff 32 distal the corresponding base 31 comprises a tapered surface 32a.

An elongate handle 35 is attached to one end plate 30. In this exemplary embodiment, handle 35 is a T-shape member configured to be grasped by a subsea ROV. Handle 35 allows the subsea ROV to position and manipulate device 10 during subsea deployment and inspection operations. In general, base 21, end plates 30, and handle 35 may be made of suitable material(s) suitable for the anticipated subsea conditions including, without limitation, aluminum, stainless steel, and carbon steel.

Referring still to FIGS. 1-4, carriage assembly 40 is configured to move axially along base 21 between ends 21a, b. In this embodiment, carriage assembly 40 includes a traveling base or block 41, a pair of mounting brackets 45 extending from base 41, a plurality of connecting rods 47 coupled to base 41, and a motor mount 50 coupled to brackets 45. In this embodiment, traveling base 41 has an upper planar surface 42 and a lower planar surface 43 oriented parallel to surface 42. Lower surface 43 faces, and is parallel to, surface 22 of base 21, and upper surface 42 faces away from base 21. Mounting brackets 45 extend downward from the lateral sides of base 41 on either side of base 21. Thus, together, base 41 and mounting brackets 45 define a generally U-shaped structure disposed about base 21.

Connecting rods 47 extending perpendicularly from upper surface 42 and a plurality of guide wheels or roller members 46 are rotatably coupled to lower surface 43. Each roller member 46 has an axis of rotation oriented perpendicular to surfaces 42, 43. In this embodiment, four roller members 46 are provided, two roller members 46 are positioned proximal one mounting bracket 45 and the other two roller members 46 are positioned proximal the other mounting bracket 45. Roller members 46 smoothly guide the movement of carriage assembly 40 along base 21. More specifically, an elongate track 36 is attached to upper surface 22 and extends axially along base 21. Track 36 has lateral sides or edges 37 that are spaced slightly above surface 22 of base 21. Each roller member 46 includes an annular recess in its outer cylindrical surface that receives and engages one edge 37. In particular, two roller members 46 engage one edge 37 and the other two roller members 46 engage the other edge 37, thereby preventing carriage assembly 40 from moving laterally relative to base 21 as well as preventing carriage assembly 40 from decoupling from track 36 and base 21.

Figure 6:
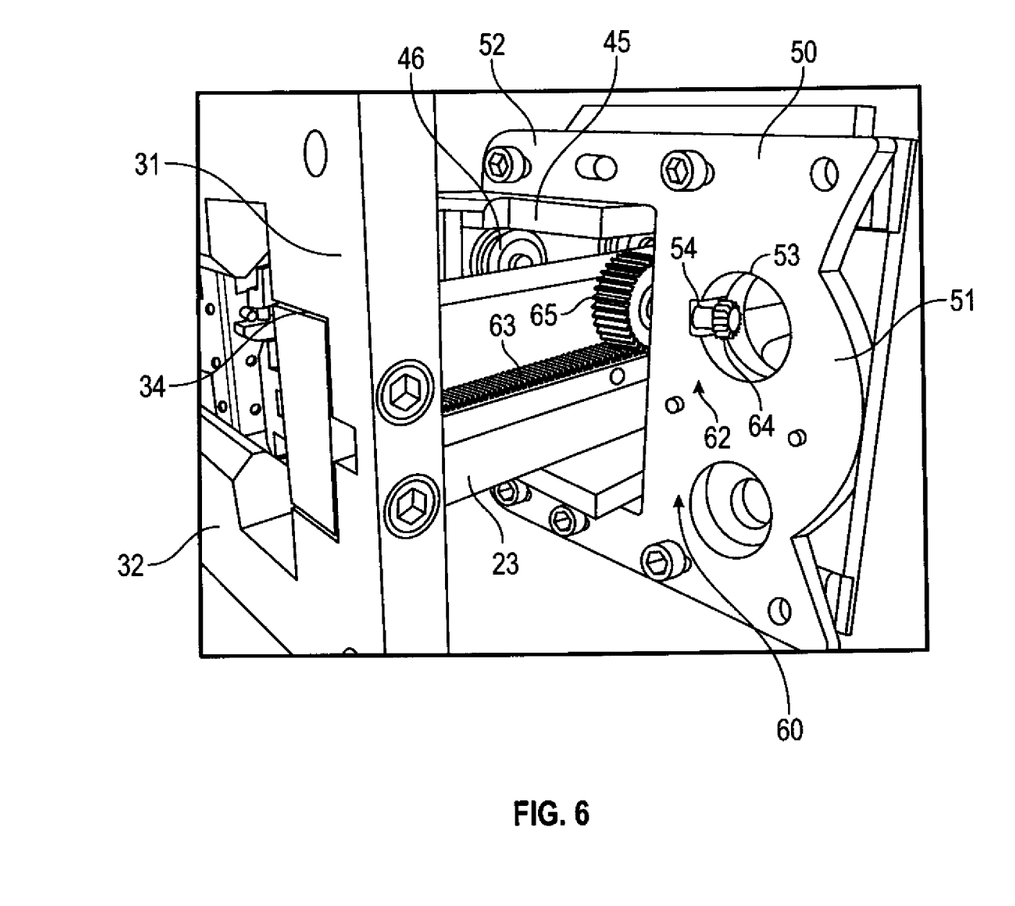
FIG. 6 is an enlarged perspective view of the ultrasonic inspection device of FIG. 1 illustrating portions of the drive system.

Referring now to FIGS. 1, 2, and 6, motor mount 50 is also a U-shaped member that straddles base 21. In particular, motor mount 50 includes a motor connection portion 51 opposed lower surface 23, and a pair of arms or connection portions 52 extending perpendicularly from the ends of portion 51. Connection portions 52 extend upward on either side of base 21, and are attached to corresponding mounting brackets 45, thereby coupling motor mount 50 to base 21. As best shown in FIG. 6, motor connection portion 51 includes an axial through bore 53 and a shaft bore 54 extending vertically from bore 53 to the upper surface of portion 51 facing lower surface 23.

Figure 3:
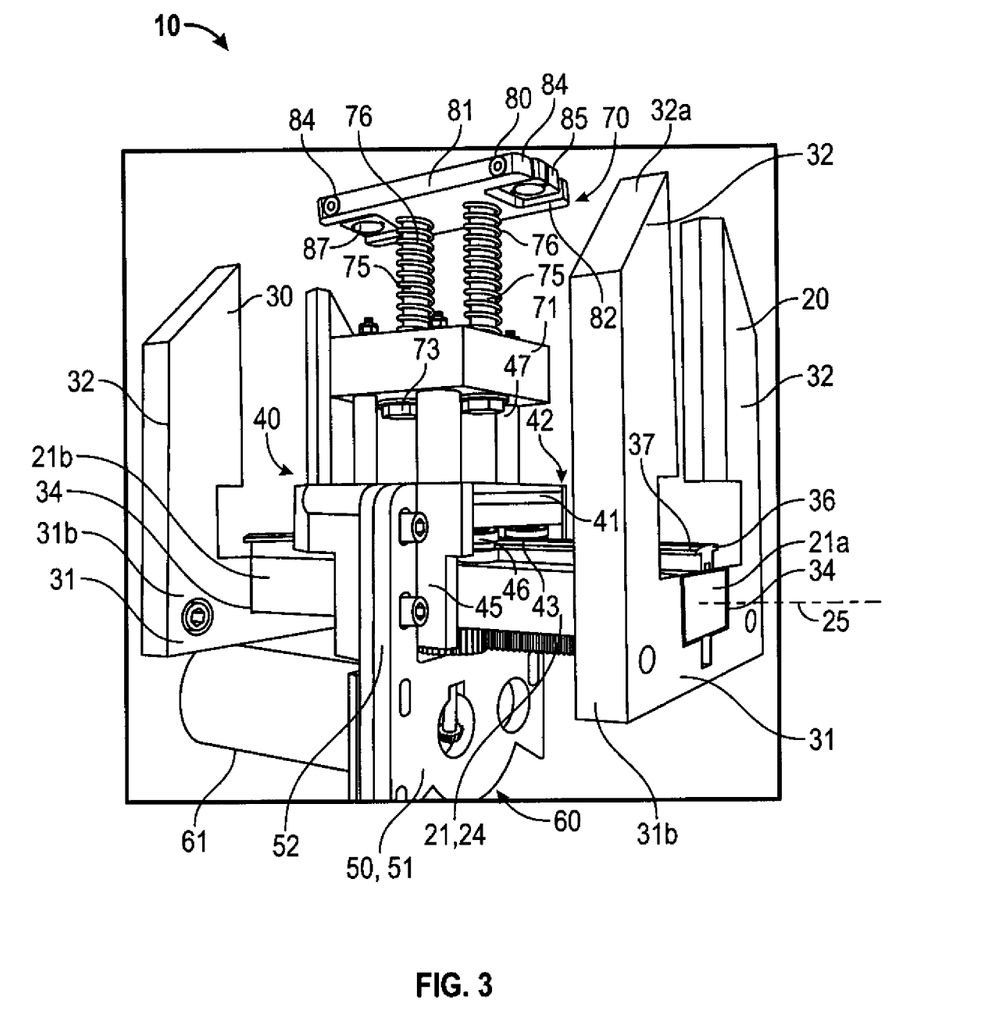
FIG. 3 is an enlarged perspective view of the ultrasonic inspection device of FIG. 1 illustrating the carriage assembly and probe suspension system.
Figure 4:
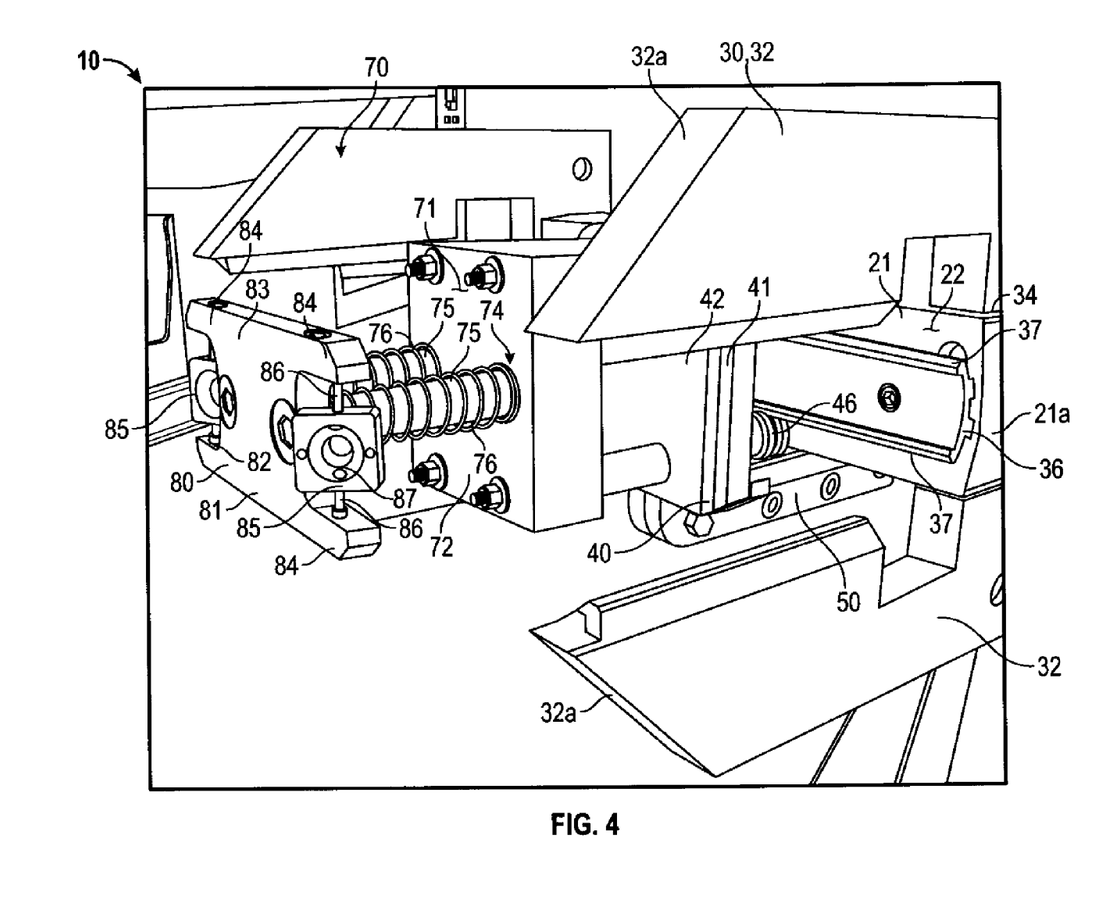
FIG. 4 is an enlarged perspective view of the ultrasonic inspection device of FIG. 1 illustrating the carriage assembly and probe suspension system.
Figure 5:
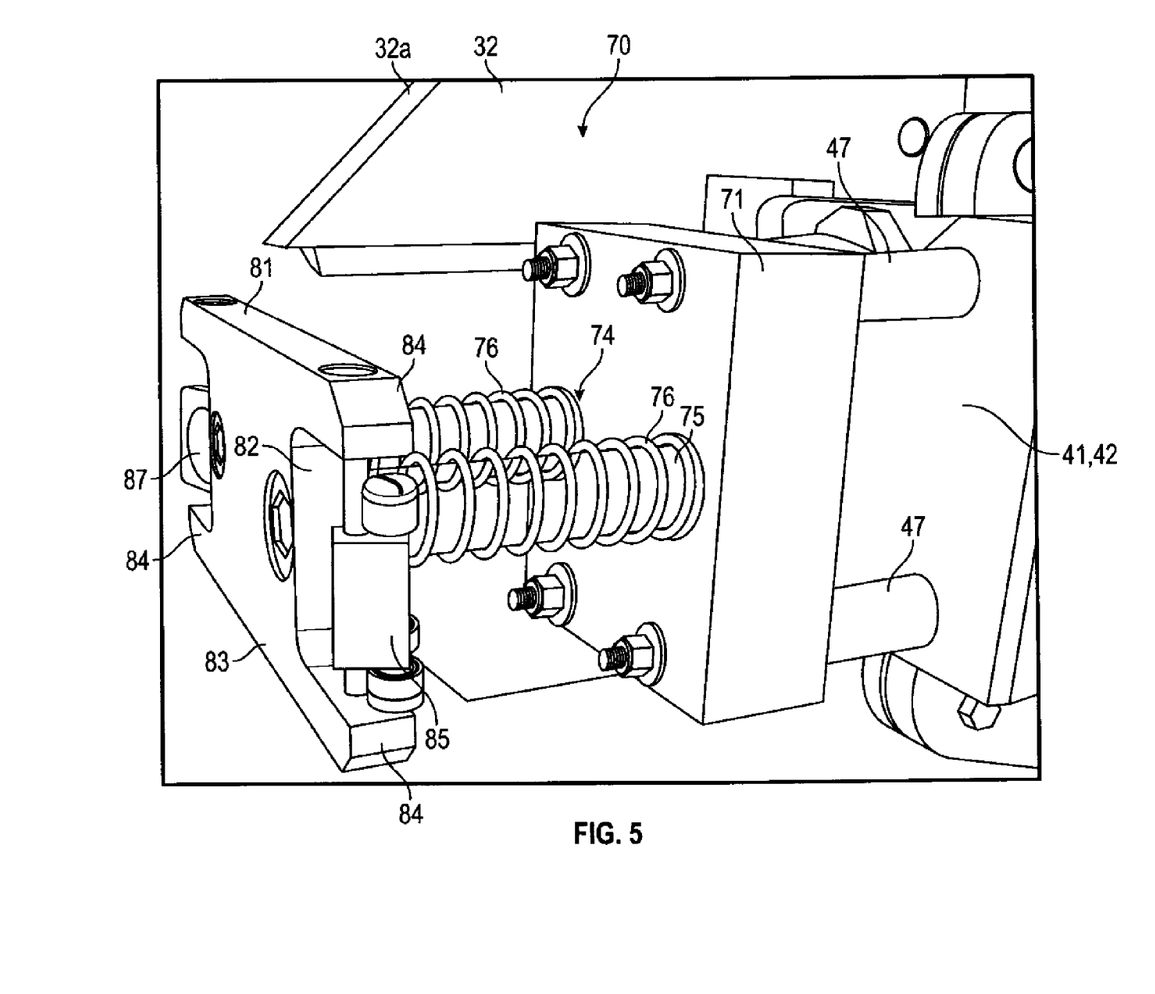
FIG. 5 is an enlarged perspective view of the ultrasonic inspection device of FIG. 1 illustrating the probe suspension system.

Referring now to FIGS. 3-5, probe suspension system 70 includes an auxiliary support block 71 attached to the upper ends of connecting rods 47, a pair of cylindrical supports 75 slidingly engaging block 71, a pair of coil springs 76 disposed about cylindrical supports 75, and a probe holder 80 attached to supports 75. For purposes of clarity, springs 76 are not shown in FIGS. 1 and 2 and probes 90 are not shown in FIGS. 3-5. Block 71 is generally rectangular member having an upper surface 72 and a lower planar surface 73, each surface 72, 73 being oriented parallel to surface 42. In this embodiment, block 71 is bolted to the upper end of each rod 47, and thus, is spaced above base 41 of carriage assembly 40. In addition, block 71 includes a pair of cylindrical through bores 74 extending between surfaces 72, 73. Each support 75 extends through and slidingly engages one bore 74. The lower end of each support 75 includes an annular flange (not shown) that engages the lower surface 73 of block 71, thereby preventing the supports 75 from being pulled completely through bores 74.

As best shown in FIGS. 1, 2, 4, and 5, probe holder 80 includes a holding block 81 and a pair of ultrasonic probe seats 85 pivotally coupled to block 81. Holding block 81 is a generally rectangular member having a recess 82 at each end and a planar upper surface 83 facing outwardly away from carriage assembly 40. Each recess 82 defines a pair of parallel arms 84 at each end of block 81. One probe seat 85 is positioned between each pair of arms 84, and is pivotally coupled thereto with two coaxially aligned pins 86. Each seat 85 includes a central receiving aperture 87 for retaining one probe 90 therein. Ultrasonic probes 90 are mounted in apertures 87 in seats 85 with a "0 degree" orientation, meaning that probes 90 are oriented such that the ultrasonic waves emitted from probes 90 will travel initially in a direction perpendicular to upper surface 83 of holding block 81. When probes 90 are mounted in apertures 87 in the 0-degree orientation, the wave transmitting/receiving end 90a of each probe 90 is positioned substantially coplanar with surface 83.

In general, ultrasonic probe 90 may be any commercially available ultrasonic probe capable of emitting and receiving ultrasonic signals. For subsea use, each probe 90 and its corresponding cable 91 (FIG. 8), which supplies power to probe 90 and communicates data and control signals to/from probe 90, are preferably water tight and rated for subsea use up to the depth at which the ultrasonic investigation is to be performed. One example of a suitable ultrasonic probe for use subsea is a deepwater immersion ultrasonic probe, operating at 5 MHz, as supplied by Phoenix Ultrasonic Systems Ltd. of Cheshire, UK.

Referring still to FIGS. 3-5, block 81 of probe holder 80 is bolted to the upper ends of supports 75, and thus, does not move rotationally or translationally relative to supports 75. However, supports 75 slidingly engage bores 74, and thus, probe holder 80 is free to move up and down relative to block 71. Each spring 76 is in compression and has an upper end engaging block 81 and a lower end engaging block 71. Thus, springs 76 bias holding block 81 away from block 71, thereby maintaining upper surface 83 of holding block 81 into contact with the object of interest being inspected as carriage assembly 40 and suspension system 70 moved linearly along the object of interest.

Referring now to FIGS. 3 and 6, drive system 60 includes a drive motor 61 and a gear assembly 62 supported on motor mount 50 of carriage assembly 40. For purposes of clarity, motor 61 is not shown in FIG. 6. In this embodiment, drive motor 61 is a deepwater rated (sealed) servo motor with encoder, such as 4,000 M servo motor supplied by Sonomatic Ltd, however, other drive motors can be employed. Gear assembly 62 translates the rotation of the motor shaft to the axial movement of carriage assembly 40 along track 36 on base 21. More specifically, gear assembly 62 includes an elongate toothed rack 63 mounted to lower surface 23 of base 21, a first gear 64 extending into through bore 53, and a second gear 65 engaging rack 63. Gears 64, 65 are mounted to opposite ends of a shaft rotatably disposed in shaft bore 54. A gear on the output shaft of motor 61 engages first gear 64 and drives the rotation of second gear 65 via the shaft extending through bore 54. As second gear 65 intermeshes and rotates relative to rack 63, carriage assembly 40 and probe suspension system 70 coupled thereto move axially between ends 21a, b of base 21.

Embodiments of apparatus and methods described herein have particular utility in examining components internal to subsea device or structure, and to determine the position and/or condition of such internal components. As examples of the many uses, the apparatus and methods described herein may be advantageously employed to determine the location of a pipeline pig that has become inoperative somewhere inside an underwater pipeline, or to determine the position of a piston housed within hydraulic cylinder or actuator. Moreover, embodiments described herein may be deployed to investigate malfunctioning equipment or to perform periodic maintenance on subsea equipment. One exemplary embodiment of a method employing the above-described device is shown in FIGS. 7-9.

Figure 7:
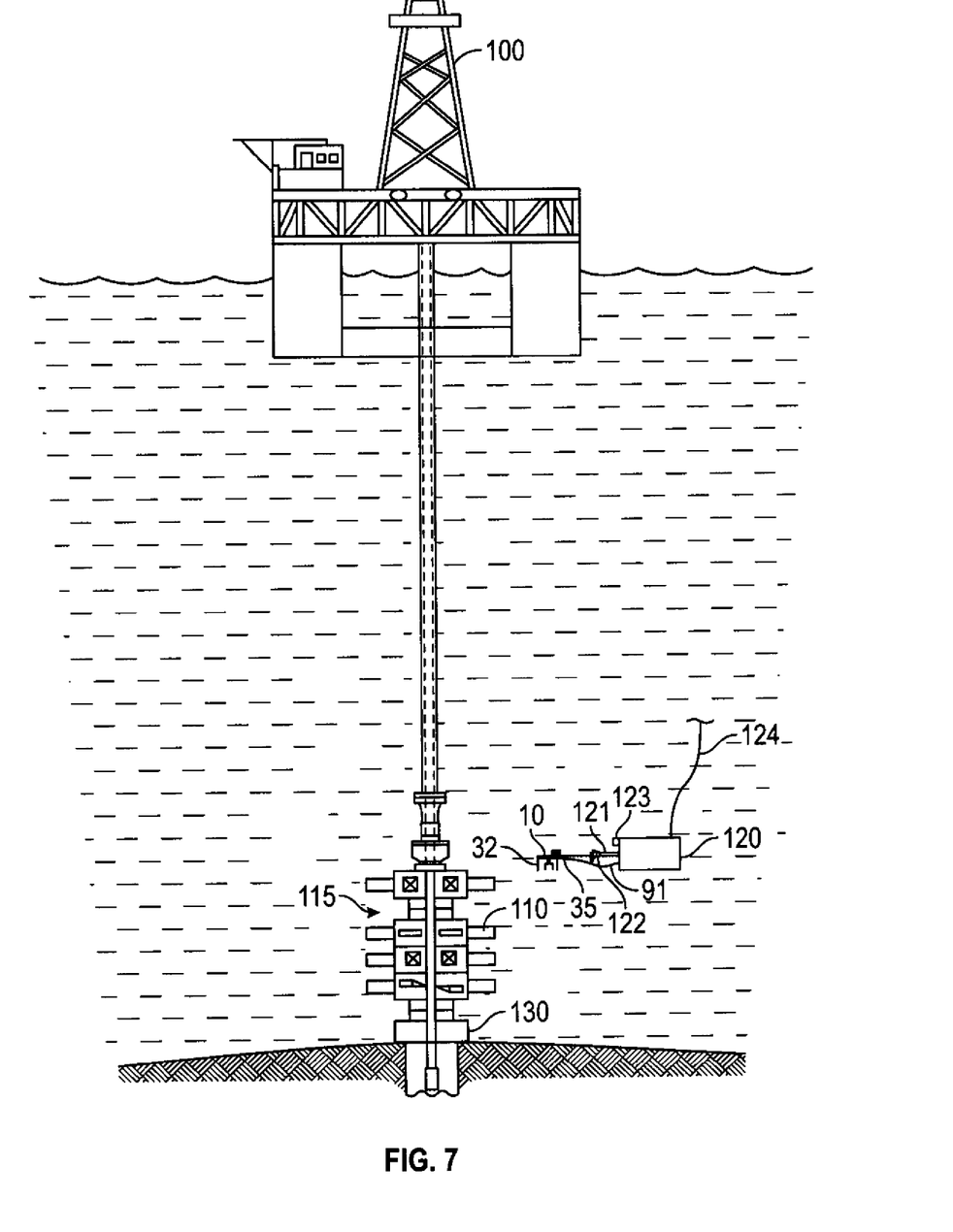
FIGS. 7-9 are schematic views of an embodiment of a method for deploying and using the ultrasonic inspection device of FIG. 1 in accordance with principles described herein.
Figure 8:
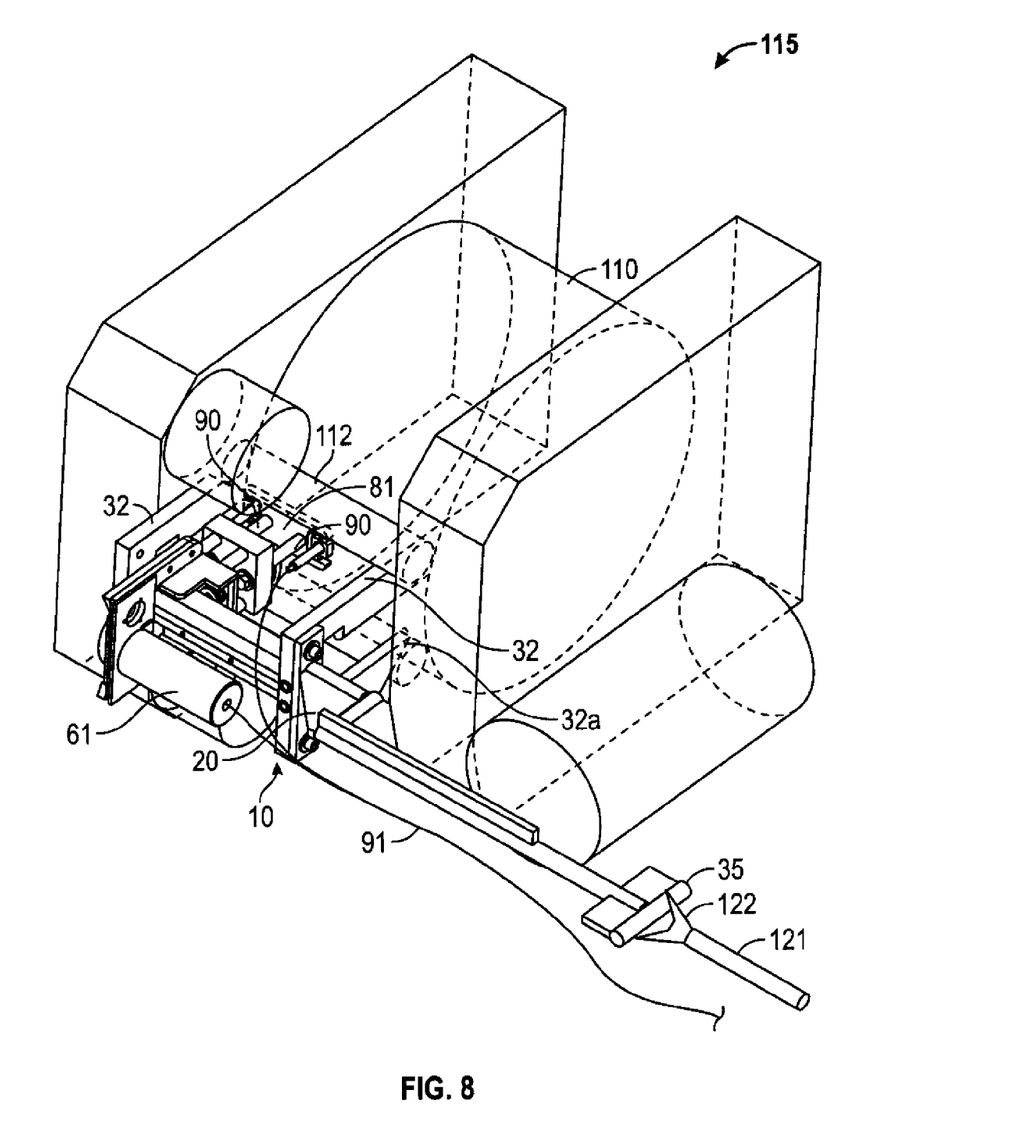
Figure 9:
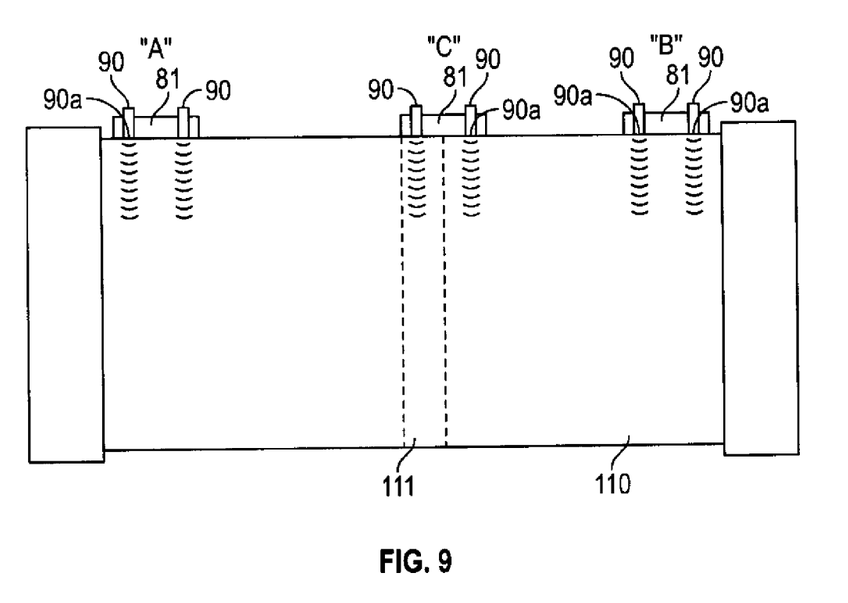

Referring now to FIGS. 7-9, device 10 is deployed subsea from a surface vessel 100 to a position adjacent an object of interest 110 to be ultrasonically inspected. In this exemplary embodiment, vessel 100 is a drilling platform and object of interest 110 is a hydraulic cylinder of a BOP stack 115 mounted to a wellhead 130 at the sea floor. BOP stack 115 includes a series of hydraulic cylinders (e.g. cylinder 110) that power rams and shears designed to shut-off the flow of hydrocarbons through BOP stack 115 in the event of a loss of well control. The position of a piston 111 within cylinder 110 is useful information as it will, in turn, identify the axial position of the corresponding ram. For subsea deployment and operation, one or more remote operated vehicles (ROVs) are preferably employed to position, manipulate, operate, and monitor device 10. In this embodiment, one ROV 120 is shown. ROV 120 includes an arm 121 having a claw 122, a subsea camera 123 for viewing the subsea operations (e.g., the relative positions of device 10 and the object of interest, the orientation of housing 40, the movement of claw 122 and arm 121, etc.), and an umbilical 124. Streaming video and/or images from camera 123 is communicated to the surface or other remote location via umbilical 124 for viewing on a live or periodic basis. Arm 121 and claw 122 are controlled via commands sent from the surface or other remote location to ROV 120 through umbilical 124.

In this example, access to cylinder 110 to be ultrasonically examined using device 10 is hampered by surrounding structures and components of BOP stack 115. In particular, as shown in FIG. 8, cylinder 110 is surrounded by circumferentially-disposed bolts 112 (two shown in FIG. 8) that block access to the walls of cylinder 110 except for wall segments that are accessible between bolts 112. Knowing the diameter of the wall of cylinder 110, and the size, position and spacing of bolts 112 allows for standoffs 32 of mount 20 to be sized to bear against adjacent bolts 112 as shown in FIG. 8.

Referring now to FIG. 8, using manipulator arm 121, ROV 120 grasps handle 35 and then positions device 10 along cylinder 110 such that tapered surfaces 32a of standoffs 32 engage bolts 112. Tapered surfaces 32a allow ROV 120 to wedge and secure mount 20 into a stationary and stable position as advantageous for the ultrasonic inspection. In other embodiments, the axial spacing between the standoffs (e.g., standoffs 32), the shape of the ends of the standoffs, and the length of the standoffs may differ from that shown in FIG. 8, those parameters being tailored so that the mount 20 can be securely braced by ROV 120 against the particular structures that are near the object that is to be ultrasonically examined, and so that the probes (e.g., probes 90) and the probe holding block (e.g., block 81) can be brought into engagement with the outer surface of the object of interest. Power is supplied to probe 90 and motor 61 via power conductors contained within probe cable 91, which is coupled to ROV 120. Similarly, control and data signals are communicated between probe 90 and ROV 120 via separate conductors contained in probe cable 91. In turn, power as well as data and control signals are communicated between ROV 120 and surface vessel 100 via ROV umbilical 124 (FIG. 7). Images generated from the reflected ultrasonic waves that are received by probes 90 are displayed to operators on display monitors on vessel 100.

When the ultrasonic examination is to begin, and with mount 20 positioned appropriately as shown in FIG. 8, probes 90 are actuated so as to begin sending pulsed, ultrasonic wave forms into cylinder 110. In a known manner, the waveform is transmitted with some refraction at the interface of differing materials and will also be reflected from objects encountered, the direction of the reflected wave dependent upon the angle of incidence. Accordingly, via internal transducers, probes 90 transform the mechanical energy from the reflected waveforms into electrical signals that are transmitted via probe cable 91 to ROV 120 and, subsequently, to vessel 100 for analysis.

Referring now to FIG. 9, drive system 60 is then used to move carriage assembly 40 and probes 90 linearly along cylinder 110. In FIG. 8, mount 20 is shown in a first position "A" at one end of its permitted distance of travel. In position A, probes 90 ultrasonically inspect the internals of cylinder 110 in that general region. After an ultrasonic inspection at position A, probes 90 are moved (to the right as shown in FIG. 9) to a second position along cylinder 110 that is preferably less than one inch from the previous position, and probes 90 will again examine the corresponding portions of cylinder 110 directly aligned with the fixed, zero-degree positions of probes 90. This process is repeated along the entire length of cylinder 110, from position A at one end of cylinder 110 to position "B" at the opposite end of cylinder 110. Embodiments of the drive systems disclosed herein (e.g., drive system 60) preferably permit fine linear movement to enable ultrasonic inspections of cylinder 110 at increments equal to 0.01 in.

At each position along cylinder 110, probes 90 transmit ultrasonic waves and receive return ultrasonic waves, which are converted to electrical signals, processed, and displayed to operators on vessel 100. As examination of cylinder 110 progresses along the entire length of travel of mount 20 from position A to position B, piston 111 is detected and its position identified at position "C," which such data then being displayed to operators on vessel 100. Thus, knowing the position of piston 111, the length of linkages between piston 111 and the ram that is actuated by piston 111, operators can determine the location of the ram. When the ultrasonic investigation is complete, ROV 120 grasps handle 35, disengages device 10 from its position adjacent cylinder 110, and returns device 10 to the surface vessel 100.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A device for conducting an ultrasonic inspection of an object of interest, the device comprising:
   a base member configured to be moved relative to the object of interest during an inspection of the object of interest;
   a track coupled to the base member;
   a carriage moveably coupled to the track;
   a drive system coupled to the carriage and configured to move the carriage linearly along the track; and
   an ultrasonic probe coupled to the carriage.

2. The device of claim 1, wherein the probe is biased away from the carriage.

3. The device of claim 2, further comprising a plurality of standoffs coupled to the base member, wherein the standoffs are configured to position the carriage a distance away from the object of interest when the probe is biased into engagement with the object of interest.

4. The apparatus of claim 1, further comprising a handle coupled to the base member, wherein the handle is configured to be manipulated by a subsea ROV.

5. The device of claim 1, wherein the drive system includes a motor coupled to the carriage.

6. The device of claim 5, wherein the drive system includes a toothed rack attached to the base member and a gear assembly that couples the motor to the toothed rack.

7. The device of claim 1, wherein the carriage includes a base and a plurality of roller members that are rotatably coupled to the base and engage the track.

8. A method for conducting a subsea ultrasonic inspection of subsea object of interest, comprising:
   (a) deploying an ultrasonic inspection device subsea, the device including a base member and an ultrasonic probe moveably coupled to the base member;
   (b) moving the base member of the ultrasonic inspection device relative to the object of interest to position the ultrasonic probe adjacent the object of interest after (a);
   (c) emitting a first ultrasonic waveform from the ultrasonic probe into the object of interest;
   (d) moving the probe linearly relative to the base member and the object of interest; and
   (e) emitting a second ultrasonic waveform from the probe into the object of interest after (c) and (d).

9. The method of claim 8, wherein the device includes a carriage moveably coupled to the base, wherein the ultrasonic probe is coupled to the carriage; and
   wherein (d) comprises moving the carriage relative to the base member and the object of interest.

10. The method of claim 9, wherein the device includes a plurality of standoffs coupled to the base member;
    wherein (b) comprises utilizing the standoffs to space the base member and the carriage from the object of interest.

11. The method of claim 8, wherein (b) comprises positioning the device with a subsea ROV.

12. The method of claim 8, further comprising:
    (f) biasing the probe into engagement with the object of interest during (c), (d), and (e).

13. The method of claim 8, wherein (a) comprises deploying the ultrasonic inspection device subsea to investigate a malfunctioning piece of subsea equipment or perform maintenance on a piece of subsea equipment.

14. An apparatus for performing an ultrasonic inspection of an object of interest, comprising:
    a base member having a longitudinal axis, a first end, a second end opposite the first end, an upper surface extending between the first end and the second end, and a lower surface extending between the first end and the second end;
    an elongate track mounted to the upper surface of the base member and oriented parallel to the longitudinal axis;
    a carriage assembly moveably coupled to the track;
    a drive system coupled to the carriage assembly and configured to move the carriage assembly along the track;
    a probe suspension system moveably coupled to the carriage assembly, the probe suspension system including a probe holder biased away from the carriage assembly;
    an ultrasonic probe mounted to the probe holder, wherein the probe holder and the ultrasonic probe are configured to be biased toward the object of interest.

15. The apparatus of claim 14, further comprising a plurality of standoffs coupled to the base member and extending upward from the upper surface of the base member.

16. The apparatus of claim 14, further comprising a handle coupled to the base member, wherein the handle is configured to be manipulated by a subsea ROV.

17. The apparatus of claim 14, wherein the carriage assembly includes a traveling base opposed the upper surface of the base member and a pair of mounting brackets extending from the base along a pair of lateral sides of the base member.

18. The apparatus of claim 17, wherein the traveling base has a lower surface coupled to a plurality of roller members that rotatably engage the track.

19. The apparatus of claim 17, wherein the carriage assembly further includes a motor mount coupled to the mounting brackets.

20. The apparatus of claim 14, wherein the drive system includes an elongate toothed rack mounted to the lower surface of the base member, a gear assembly coupled to the toothed rack, and a motor coupled to the carriage assembly.

* * * * *